United States Patent
Hinamoto et al.

(10) Patent No.: US 9,271,901 B2
(45) Date of Patent: Mar. 1, 2016

(54) ONE-PART DENTAL ADHESIVE COMPOSITION

(75) Inventors: Ai Hinamoto, Okayama (JP); Naoki Nishigaki, Kurashiki (JP); Naofumi Murata, Kawaguchi (JP)

(73) Assignee: KURARAY NORITAKE DENTAL INC., Kurashiki-shi (JP)

(*) Notice: Subject to any disclaimer, the term of this patent is extended or adjusted under 35 U.S.C. 154(b) by 543 days.

(21) Appl. No.: 13/636,167

(22) PCT Filed: Mar. 25, 2011

(86) PCT No.: PCT/JP2011/001792
§ 371 (c)(1),
(2), (4) Date: Sep. 20, 2012

(87) PCT Pub. No.: WO2011/121966
PCT Pub. Date: Oct. 6, 2011

(65) Prior Publication Data
US 2013/0012615 A1    Jan. 10, 2013

(30) Foreign Application Priority Data
Mar. 30, 2010   (JP) .................. 2010-079384

(51) Int. Cl.
*A61K 6/083*   (2006.01)
*A61K 6/00*    (2006.01)

(52) U.S. Cl.
CPC ............. *A61K 6/0023* (2013.01); *A61K 6/0052* (2013.01); *A61K 6/083* (2013.01)

(58) Field of Classification Search
CPC ............................. A61K 6/083; A61K 6/0052
USPC .......................................................... 523/116
See application file for complete search history.

(56) References Cited

U.S. PATENT DOCUMENTS

| | | | |
|---|---|---|---|
| 4,909,887 A | 3/1990 | Wagenknecht et al. | |
| 5,061,184 A * | 10/1991 | Yamazaki et al. | 433/228.1 |
| 7,615,582 B2 | 11/2009 | Nakatsuka et al. | |
| 7,655,722 B2 | 2/2010 | Nakatsuka et al. | |
| 2010/0130682 A1 | 5/2010 | Hinamoto et al. | |
| 2011/0124763 A1* | 5/2011 | Hinamoto et al. | 522/28 |

FOREIGN PATENT DOCUMENTS

| | | |
|---|---|---|
| JP | 62 205004 | 9/1987 |
| JP | 1 152179 | 6/1989 |
| JP | 1 502121 | 7/1989 |
| JP | 10 87671 | 4/1998 |
| JP | 2003 13012 | 1/2003 |
| JP | 2003 81731 | 3/2003 |
| JP | 2003 89759 | 3/2003 |
| JP | 2003 105272 | 4/2003 |
| WO | 2005 060920 | 7/2005 |
| WO | 2006 115065 | 11/2006 |
| WO | 2008 087977 | 7/2008 |
| WO | WO 2010008077 A1 * | 1/2010 ................ C08F 2/50 |

OTHER PUBLICATIONS

Kadoma, Y., et al., "Bonding durability against water of fluorine-containing resin for precious metal alloys," Dental Materials Journal, vol. 28, No. 5, pp. 642 to 648, (2009).

Oshikawa, A., et al., "A Study on the Properties of Adhesion and Durability of Dental Adhesive," The Journal of the Japanese Society for Dental Materials and Devices, vol. 27, No. 3, pp. 246 to 255, (2008).

International Search Report Issued Apr. 19, 2011 in PCT/JP11/001792 Filed Mar. 25, 2011.

* cited by examiner

Primary Examiner — Michael Pepitone
(74) Attorney, Agent, or Firm — Oblon, McClelland, Maier & Neustadt, L.L.P.

(57) ABSTRACT

The present invention provides a one-part dental adhesive composition that exhibits excellent adhesive property and bond durability to a tooth structure (particularly dentin) and has high stability to ambient light, in which respective components have been mixed uniformly. The present invention is a one-part dental adhesive composition including a polymerizable monomer (A) having an acidic group, a polymerizable monomer (B) having a fluorocarbon group represented by the general formula (1), water (C), and a polymerization initiator (D). A content of the polymerizable monomer (A) having an acidic group is 5.5 to 35 parts by weight in 100 parts by weight of the total amount of polymerizable monomers. (In the formula, $R^1$ denotes a hydrogen atom or a methyl group, and Rf denotes a fluoroalkyl group having 1 to 20 carbon atoms.)

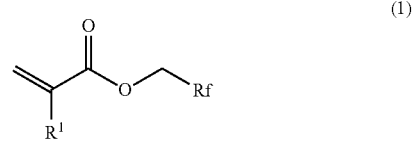

(1)

9 Claims, No Drawings

ONE-PART DENTAL ADHESIVE COMPOSITION

CROSS REFERENCE TO RELATED APPLICATIONS

This application is a National Stage entry under 35 U.S.C. 371 of PCT/JP11/001792, filed on Mar. 25, 2011, the text of which is incorporated by reference, and claims priority to Japanese Patent Application No. 2010-079384, filed on Mar. 30, 2010, the entire content of which is incorporated herein by reference.

TECHNICAL FIELD

The present invention relates to a composition that includes polymerizable monomers and that is used as a one-part dental adhesive. Specifically, the present invention relates to a one-part dental adhesive composition that is used for bonding a dental restorative material, such as a dental composite resin, a dental compomer and a dental resin cement, to a tooth structure.

BACKGROUND ART

When a lost part of a tooth is filled or covered with a restorative material, generally a dental adhesive is used. When such a dental adhesive is allowed to act on a tooth structure, particularly on dentin, it is important for the dental adhesive to have an decalcifying effect that allows a dentin surface to be dissolved with an acidic component, a penetration effect that allows a monomer component to penetrate into a collagen layer of the dentin, and a curing effect that allows the monomer component thus penetrated to solidify to form a hybrid layer (hereinafter also referred to as a "resin-impregnated layer") with collagen.

It has been studied so far to simplify the form of application of the dental adhesive from a three-component three-step type in which the aforementioned decalcifying effect, penetration effect, and curing effect are applied sequentially, to a two-component two-step type in which the decalcifying effect and the penetration effect are integrated, and further to a one-part one-step type in which the decalcifying effect, penetration effect, and curing effect are all combined together. Particularly in recent years, developments have progressed on the one-part one-step dental adhesive that makes the bonding work easy and fast and that is resistant to contamination by saliva and blood.

For example, Patent Literature 1 discloses a one-part dental adhesive composition including a hydrophobic polymerizable monomer having an acidic group, a water-soluble polymerizable monomer, water, a photopolymerization initiator, aromatic tertiary amine having an electron-withdrawing group, a crosslinkable polymerizable monomer, and a basic compound for producing a water-soluble salt through a reaction with a part of the hydrophobic polymerizable monomer having an acidic group. According to Patent Literature 1, it is possible to obtain a composition that can achieve high adhesive property even when no pretreatment is applied to the tooth structure, and that also has excellent storage stability. However, although having excellent initial adhesive property, this dental adhesive composition may cause an adhesive layer and a resin-impregnated layer to be degraded because of water absorption. Thus, its long-term bond durability is left to be improved.

As an adhesive composition that exhibits excellent adhesive property over a long period of time, Patent Literature 2 discloses an adhesive composition for a biomaterial, including a polymerizable monomer having a fluorocarbon group. The literature describes that a cured product obtained by polymerizing a polymerizable monomer having a fluorocarbon group has excellent water absorption rate and dimensional stability. It further describes that a mixed composition of polymer powder obtained by polymerizing a polymerizable monomer having a fluorocarbon group, a polymerizable monomer having a fluorocarbon group, a polymerizable monomer having an acidic group, and a polymerization initiator has excellent adhesive property to a tooth structure.

As a dental composition including a polymerizable monomer having a fluorocarbon group, Patent Literature 3 discloses a composition including a polymerizable monomer having a fluorocarbon group and at least two polymerizable groups, a hydrophilic polymerizable monomer, and a polymerization initiator. The literature describes that this composition can be cured through polymerization in a short period of time, and has satisfactory affinity to a tooth structure and an adhesive material while exhibiting excellent water repellence and coloration resistance, and excellent adhesive property can be achieved.

CITATION LIST

Patent Literature

PTL 1: WO 2005/060920

PTL 2: JP 1 (1989)-152179 A

PTL 3: JP 2003-81731 A

SUMMARY OF INVENTION

Technical Problem

To enhance the bond durability of a one-part dental adhesive composition, it also is considered using such a polymerizable monomer having a fluorocarbon group as those disclosed in Patent Literatures 2 and 3. However, the present inventors found, through their studies, that when a polymerizable monomer having a fluorocarbon group is used as a component of a one-part dental adhesive composition, there arises a problem that the composition becomes nonuniform or unstable to ambient light.

Thus, the present invention is intended to provide a one-part dental adhesive composition that exhibits excellent adhesive property and bond durability to a tooth structure (particularly dentin) and has high stability to ambient light, in which respective components have been mixed uniformly.

Solution to Problem

The present invention is a one-part dental adhesive composition comprising a polymerizable monomer (A) having an acidic group, a polymerizable monomer (B) having a fluorocarbon group represented by the following general formula (1), water (C), and a polymerization initiator (D). A content of the polymerizable monomer (A) having an acidic group is 5.5 to 35 parts by weight in 100 parts by weight of the total amount of polymerizable monomers.

[Chemical Formula 1]

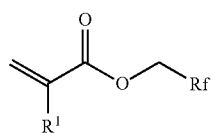

(In the formula, R1 denotes a hydrogen atom or a methyl group, and Rf denotes a fluoroalkyl group having 1 to 20 carbon atoms.)

Preferably, a content of the polymerizable monomer (B) having a fluorocarbon group is 0.5 to 10 parts by weight in 100 parts by weight of the total amount of polymerizable monomers.

Preferably, the one-part dental adhesive composition of the present invention further includes 10 to 50 parts by weight of a polymerizable monomer (E) having one polymerizable group and at least one hydroxyl group in 100 parts by weight of the total amount of polymerizable monomers. Preferably, the one-part dental adhesive composition of the present invention further includes a polymerizable monomer (F) having two polymerizable groups and two hydroxyl groups represented by the following general formula (2). Preferably, a content of the polymerizable monomer (F) is 5 to 20 parts by weight in 100 parts by weight of the total amount of polymerizable monomers.

[Chemical Formula 2]

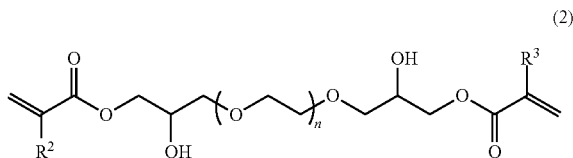

(In the formula, $R^2$ and $R^3$ each denote independently a hydrogen atom or a methyl group, and n denotes an integer of 1 to 5.)

Preferably, the one-part dental adhesive composition of the present invention further includes 20 to 60 parts by weight of a crosslinkable polymerizable monomer (G), other than the polymerizable monomer (F) having two polymerizable groups and two hydroxyl groups represented by the general formula (2), in 100 parts by weight of the total amount of polymerizable monomers.

Preferably, a content of the polymerization initiator (D) is 0.001 to 20 parts by weight with respect to 100 parts by weight of the total amount of polymerizable monomers. Preferably, the polymerization initiator (D) is a bisacylphosphine oxide represented by the following general formula (3).

[Chemical formula 3]

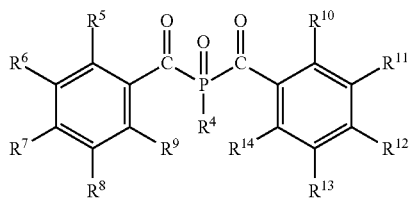

(In the formula, $R^4$ denotes an alkyl group, an alkenyl group, an alkynyl group, an aryl group, an alkoxy group, an acyl group or an acyloxy group, and $R^5$ to $R^{14}$ each denote independently a hydrogen atom, a halogen atom, an alkyl group, an alkenyl group, an alkynyl group, an aryl group, an alkoxy group, an acyl group or an acyloxy group.)

Preferably, the one-part dental adhesive composition of the present invention includes an organic solvent (H). Preferably, the one-part dental adhesive composition of the present invention includes a polymerization accelerator (I). Preferably, the one-part dental adhesive composition of the present invention includes a filler (J).

Advantageous Effects of Invention

According to the present invention, it is possible to obtain a one-part dental adhesive composition having high stability to ambient light. Thus, use of the dental adhesive composition of the present invention makes it possible to ensure sufficiently the working time, and the tooth structure treatment time necessary for decalcifying and penetration effects. Moreover, the dental adhesive composition of the present invention exhibits excellent adhesive property and bond durability to a tooth structure (particularly dentin), and is useful for bonding a dental restorative material to the tooth structure. Furthermore, since the respective components have been mixed uniformly in the dental composition of the present invention, the work of mixing uniformly the respective components at the time of use is unnecessary. Therefore, the dental composition of the present invention can be used easily.

DESCRIPTION OF EMBODIMENTS

The one-part dental adhesive composition of the present invention includes, as essential components, the polymerizable monomer (A) having an acidic group, the polymerizable monomer (B) having a fluorocarbon group represented by the general formula (1), the water (C), and the polymerization initiator (D). First, these essential components are described.

Polymerizable Monomer (A) Having an Acidic Group

The polymerizable monomer (A) having an acidic group is a component having an acid-etching effect and a primer treatment effect and providing the composition with a decalcifying effect and a penetration effect. Moreover, the polymerizable monomer (A) having an acidic group is polymerizable and also provides a curing effect. By including the polymerizable monomer (A) having an acidic group, the composition can function as a one-part dental adhesive and have enhanced adhesive property and bond durability to a tooth structure.

The polymerizable monomer (A) having an acidic group can be used alone or two or more types thereof can be used in suitable combination. The polymerizable monomer (A) having an acidic group is not particularly limited. Examples thereof include a monofunctional polymerizable monomer having one carboxyl group or an acid anhydride group thereof in the molecule, a monofunctional polymerizable monomer having a plurality of carboxyl groups or an acid anhydride group thereof in the molecule, and a monofunctional polymerizable monomer having a phosphinyl group or phosphono group in the molecule (also referred to as a monofunctional radical polymerizable phosphoric acid ester).

Examples of the monofunctional polymerizable monomer having one carboxyl group or an acid anhydride group thereof in the molecule include (meth)acrylic acid, N-(meth)acryloylglycine, N-(meth)acryloylaspartic acid, 2-(meth)acryloyloxyethyl hydrogen succinate, 2-(meth)acryloyloxyethyl hydrogen phthalate, 2-(meth)acryloyloxyethyl hydrogen malate, O-(meth)acryloyltyrosine, N-(meth)acryloyltyrosine, N-(meth)acryloylphenylalanine, N-(meth)acryloyl-p- aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid, and compounds obtained by converting the carboxyl group of these compounds into an acid anhydride group.

Examples of the monofunctional polymerizable monomer having a plurality of carboxyl groups or an acid anhydride group thereof in the molecule include 11-(meth)acryloyloxyundecane-1,1-dicarboxylic acid, 10-(meth)acryloyloxydecane-1,1-dicarboxylic acid, 12-(meth)acryloyloxydodecane-1,1-dicarboxylic acid, 6-(meth)acryloyloxyhexane-1,1-dicarboxylic acid, 2-(meth)acryloyloxyethyl-3'-methacryloyloxy-2'-(3,4-dicarboxybenzoyloxy)propyl succinate, 4-(meth)acryloyloxyethyl trimellitate anhydride, 4-(meth)acryloyloxyethyl trimellitate, 4-(meth)acryloyloxybutyl trimellitate, 4-(meth)acryloyloxyhexyl trimellitate, 4-(meth)acryloyloxydecyl trimellitate, 6-(meth)acryloyloxyethylnaphthalene-1,2,6-tricarboxylic acid, 6-(meth)acryloyloxyethylnaphthalene-1,2,6-tricarboxylic acid anhydride, 6-(meth)acryloyloxyethylnaphthalene-2,3,6-tricarboxylic acid anhydride, 4-(meth)acryloyloxyethylcarbonylpropionoyl-1,8-naphthalic acid anhydride, 4-(meth)acryloyloxyethylnaphthalene-1,8-tricarboxylic acid anhydride, 9-(meth)acryloyloxynonane-1,1-dicarboxylic acid, 13-(meth)acryloyloxytridecane-1,1-dicarboxylic acid, and 11-(meth)acrylamideundecane-1,1-dicarboxylic acid.

Examples of the monofunctional polymerizable monomer having a phosphinyl group or phosphono group in the molecule include 2-(meth)acryloyloxyethyl dihydrogen phosphate, 2-(meth)acryloyloxyethylphenyl hydrogen phosphate, 10-(meth)acryloyloxydecyl dihydrogen phosphate, 6-(meth)acryloyloxyhexyl dihydrogen phosphate, 2-(meth)acryloyloxyethyl-2-bromoethyl hydrogen phosphate, 2-(meth)acrylamideethyl dihydrogen phosphate, and 6-(meth)acryloyloxyhexyl phosphonoacetate.

Examples of other monofunctional polymerizable monomer having an acidic group include a monofunctional polymerizable monomer having a sulfo group in the molecule such as 2-(meth)acrylamide-2-methylpropanesulfonic acid and 10-sulfodecyl(meth)acrylate.

As the polymerizable monomer (A) having an acidic group, 10-(meth)acryloyloxydecyl dihydrogen phosphate, 6-(meth)acryloyloxyhexyl dihydrogen phosphate, 4-(meth)acryloyloxyethyl trimellitate, and 6-(meth)acryloyloxyhexyl phosphonoacetate are preferable among the examples mentioned above, and 10-(meth)acryloyloxydecyl dihydrogen phosphate, 4-(meth)acryloyloxyethyl trimellitate, and 6-(meth)acryloyloxyhexyl phosphonoacetate are particularly preferable.

5.5 to 35 parts by weight of the polymerizable monomer (A) having an acidic group is added in 100 parts by weight of the total amount of polymerizable monomers. When the amount of the polymerizable monomer (A) having an acidic group to be added is less than 5.5 parts by weight, the acid-etching effect and the primer treatment effect are not obtained sufficiently. Therefore, the amount preferably is at least 7 parts by weight. On the other hand, when the amount of the polymerizable monomer (A) having an acidic group to be added exceeds 35 parts by weight, the composition becomes nonuniform and the container accommodating the adhesive needs to be shaken before the application of the adhesive, impairing the advantageous simplicity of the one-part adhesive. Furthermore, sufficient curability may not be obtained, and the bond durability may be reduced because the cured product absorbs an increased amount of water.

In the present invention, the total amount of polymerizable monomers indicates the total amount of monomer components to be polymerized by the polymerization initiator (D), that is, the total amount of the polymerizable monomer (A) having an acidic group, the polymerizable monomer (B) having a fluorocarbon group, the polymerizable monomer (E) having one polymerizable group and at least one hydroxyl group, the polymerizable monomer (F) having two polymerizable groups and two hydroxyl groups, the crosslinkable polymerizable monomer (G), etc.

Polymerizable Monomer (B) Having a Fluorocarbon Group

The polymerizable monomer (B) having a fluorocarbon group represented by the following general formula (1) is a component that provides the composition with curability, improves the water absorption rate and dimensional stability of a cured product of the composition, and enhances the bond durability. Among polymerizable monomers having a fluorocarbon group, the polymerizable monomer (B) having a fluorocarbon group represented by the following general formula (1) is combined with the above-specified amount of the polymerizable monomer (A) having an acidic group and the water (C), so that the stability to ambient light, adhesive property and bond durability of the composition are increased in a balanced manner.

[Chemical Formula 4]

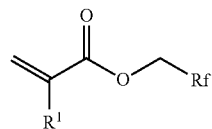

(1)

In the general formula (1), Rf is a fluoroalkyl group having 1 to 20, preferably 1 to 10, more preferably 1 to 5 carbon atoms. The number of fluorine atoms that the fluoroalkyl group has is not particularly limited as long as an hydrogen atom of the alkyl group is substituted by at least one fluorine atom. A part of or all of the hydrogen atoms of the alkyl group may be substituted by fluorine atoms.

In the general formula (1), $R^1$ denotes a hydrogen atom or a methyl group. From the viewpoint of stimulativeness to a biological body in the case where a polymerizable moiety is detached, a methyl group is preferable.

The polymerizable monomer (B) having a fluorocarbon group can be used alone or two or more types thereof can be used in suitable combination. Examples of the polymerizable monomer (B) having a fluorocarbon group include trifluoroethyl(meth)acrylate, tetrafluoropropyl(meth)acrylate, pentafluoropropyl(meth)acrylate, octafluoropentyl(meth)acrylate, and heptadecafluorononyl(meth)acrylate.

The amount of the polymerizable monomer (B) having a fluorocarbon group to be added is not particularly limited. When the amount of the polymerizable monomer (B) to be added is too small, the effect of enhancing the bond durability by the polymerizable monomer (B) may not be obtained. Moreover, coloration resistance may be lowered. On the other hand, when the amount of the polymerizable monomer (B) to be added is too large, the decalcifying effect and penetration effect of the composition may be lowered and the bond strength may be reduced. Therefore, the amount of the polymerizable monomer (B) to be added is preferably 0.5 to 10 parts by weight, more preferably 0.5 to 5 parts by weight, in 100 parts by weight of the total amount of polymerizable monomers.

Water (C)

The water (C) is a component that enhances the adhesive property and bond durability of the composition to a tooth structure. Preferably, water (C) is free from impurities that have adverse effects, and distilled water or ion exchanged water is preferable. The water (C) may be used alone, or it may be used in the form of a mixed solvent of the water (C) and the organic solvent (H) that will be described later.

Preferably, the amount of the water (C) to be added is 5 to 500 parts by weight with respect to 100 parts by weight of the total amount of polymerizable monomers. When the amount of the water (C) to be added is less than 5 parts by weight, the stability to ambient light may be lowered, and the penetrability of the polymerizable monomers into a collagen layer of dentin may be insufficient and the bond strength may be reduced. The amount of the water (C) to be added is more preferably 7 parts by weight or more, still more preferably 8 parts by weight or more, and most preferably 10 parts by weight or more. On the other hand, when the amount of the water (C) to be added exceeds 500 parts by weight, the polymerizability of the polymerizable monomers may be deteriorated, both the bond strength and bond durability may be reduced, and the uniformity of the composition may be impaired. The amount of the water (C) to be added is more preferably 100 parts by weight or less.

Polymerization Initiator (D)

The polymerization initiator (D) is a component that accelerates the curing of the composition through polymerization. The polymerization initiator (D) can be selected from polymerization initiators commonly used in the industrial field. Among them, a polymerization initiator used for dental applications is used preferably. Particularly, a photopolymerization initiator and a chemical polymerization initiator are used alone, or two or more types thereof are used in suitable combination.

Examples of the photopolymerization initiator include (bis)acylphosphine oxides, water-soluble acylphosphine oxides, thioxanthones or the quaternary ammonium salts of thioxanthones, ketals, α-diketones, coumarins, anthraquinones, benzoin alkyl ether compounds, and α-amino ketone compounds.

Preferably, among these photopolymerization initiators, at least one selected from the group consisting of (bis)acylphosphine oxides, salts thereof, α-diketones, and coumarin compounds is used. This makes it possible to obtain a composition that has excellent photocurability in visible and near-ultraviolet ranges and sufficiently high photocurability regardless of which light source among a halogen lamp, light-emitting diode (LED), and xenon lamp is used.

Examples of acylphosphine oxides used as the photopolymerization initiator include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl)phosphonate.

An example of the bisacylphosphine oxides used as the photopolymerization initiator is a bisacylphosphine oxide represented by the following general formula (3).

[Chemical Formula 5]

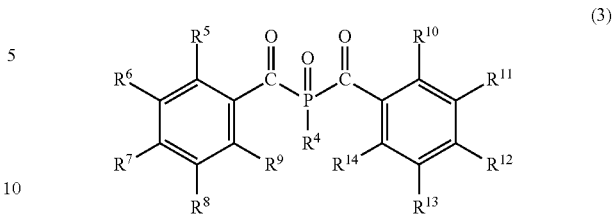

(3)

In the formula, $R^4$ denotes an alkyl group, an alkenyl group, an alkynyl group, an aryl group, an alkoxy group, an acyl group or an acyloxy group, and $R^5$ to $R^{14}$ each denote independently a hydrogen atom, a halogen atom, an alkyl group, an alkenyl group, an alkynyl group, an aryl group, an alkoxy group, an acyl group or an acyloxy group.

Alkyl groups having 1 to 10 carbon atoms are preferable as the alkyl groups denoted as $R^4$ to $R^{14}$, and examples thereof include a methyl group, ethyl group, n-propyl group, isopropyl group, cyclopropyl group, n-butyl group, isobutyl group, sec-butyl group, tert-butyl group, cyclobutyl group, n-pentyl group, isopentyl group, neopentyl group, tert-pentyl group, 2,4,4-trimethylpentyl group, cyclopentyl group, n-hexyl group, isohexyl group, cyclohexyl group, n-heptyl group, cycloheptanyl group, n-octyl group, 2-ethylhexyl group, cyclooctanyl group, n-nonyl group, cyclononanyl group, and n-decyl group.

Alkenyl groups having 2 to 10 carbon atoms are preferable as the alkenyl groups denoted as $R^4$ to $R^{14}$, and examples thereof include a vinyl group, allyl group, methylvinyl group, propenyl group, butenyl group, pentenyl group, hexenyl group, cyclopropenyl group, cyclobutenyl group, cyclopentenyl group, and cyclohexenyl group.

Alkynyl groups having 2 to 10 carbon atoms are preferable as the alkynyl groups denoted as $R^4$ to $R^{14}$, and examples thereof include an ethynyl group, 1-propynyl group, 2-propynyl group, 1-butynyl group, 1-methyl-2-propynyl group, 2-butynyl group, 3-butynyl group, 1-pentynyl group, 1-ethyl-2-propynyl group, 2-pentynyl group, 3-pentynyl group, 1-methyl-2-butynyl group, 4-pentynyl group, 1-methyl-3-butynyl group, 2-methyl-3-butynyl group, 1-hexynyl group, 2-hexynyl group, 1-ethyl-2-butynyl group, 3-hexynyl group, 1-methyl-2-pentynyl group, 1-methyl-3-pentynyl group, 4-methyl-1-pentynyl group, 3-methyl-1-pentynyl group, 5-hexynyl group, and 1-ethyl-3-butynyl group.

Aryl groups having 6 to 30 carbon atoms are preferable as the aryl groups denoted as $R^4$ to $R^{14}$, and examples thereof include a phenyl group, o-tolyl group, m-tolyl group, p-tolyl group, xylyl group, mesityl group, naphthyl group, and anthracenyl group. These aryl groups further may include an alkyl group, alkoxy group, alkenyl group, and alkynyl group.

Alkoxy groups having 1 to 10 carbon atoms are preferable as the alkoxy groups denoted as $R^4$ to $R^{14}$, and examples thereof include a methoxy group, ethoxy group, n-propoxy group, isopropoxy group, cyclopropyropoxy group, n-butoxy group, isobutoxy group, sec-butoxy group, tert-butoxy group, cyclobutoxy group, and cyclohexyloxy group.

Acyl groups having 1 to 10 carbon atoms are preferable as the acyl groups denoted as $R^4$ to $R^{14}$, and examples thereof include: formyl groups; alkylcarbonyl groups having 2 to 10 carbon atoms such as an acetyl group, propionyl group, butyryl group, isobutyryl group, valeryl group, pivaloyl group, hexanoyl group, heptanoyl group, octanoyl group, and decenoyl group; arylcarbonyl groups having 7 to 10 carbon atoms such as a benzoyl group; and arylalkylcarbonyl groups having 8 to 10 carbon atoms such as a benzylcarbonyl group.

Acyloxy groups having 1 to 10 carbon atoms are preferable as the acyloxy groups denoted as $R^4$ to $R^{14}$, and examples thereof include groups in which one oxygen atom is bonded to each of the groups described above as examples of the acyl groups.

Examples of halogen atoms denoted as $R^5$ to $R^{14}$ include a fluorine atom, chlorine atom, and bromine atom. Among these, a chlorine atom is preferable.

An alkyl group and aryl group each are preferable as $R^4$. A hydrogen atom, halogen atom, alkyl group, and alkoxy group are preferable as W to $R^{14}$.

Specific examples of the bisacylphosphine oxide represented by the formula (3) include bis-(2,6-dichlorobenzoyl) phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl) phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, and (2,5,6-trimethylbenzoyl)-2,4,4-trimethylpentylphosphine oxide.

Examples of the α-diketones used as the photopolymerization initiator include diacetyl, dibenzyl, camphorquinone, 2,3-pentadione, 2,3-octadione, 9,10-phenanthrenequinone, 4,4'-oxybenzyl, and acenaphthenequinone. Among these, camphorquinone is particularly preferable from the viewpoint of having the maximum absorption wavelength in the visible light range.

Examples of the coumarin compound used as the aforementioned photopolymerization initiator include compounds described in JP 9 (1997)-3109 A and JP 10 (1998)-245525 A such as 3,3'-carbonylbis(7-diethylamino)coumarin, 3-(4-methoxybenzoyl)coumarin, 3-thienoyl coumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl) coumarin, 3-(p-nitrobenzoyl)coumarin, 3-benzoyl-8-methoxycoumarin, 3,5-carbonylbis(7-methoxycoumarin), 3-benzoyl-6-bromocoumarin, 3,3'-carbonylbiscoumarin, 3-benzoyl-7-dimethylaminocoumarin, 3-benzoylbenzo[f] coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f]coumarin, 7-methoxy-3-(p-nitrobenzoyl)coumarin, 3-(p-nitrobenzoyl) coumarin, 3-benzoyl-8-methoxycoumarin, 3-benzoyl-6-nitrocoumarin, 3-benzoyl-7-diethylaminocoumarin, 7-dimethylamino-3-(4-methoxybenzoyl)coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo[f]coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazole-2-ilidene) acetyl]coumarin, 3-[(1-methylnaphtho[1,2-d]thiazole-2-ilidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazoyl)-7-(diethylamino)coumarin, 3-(2-benzothiazoyl)-7-(dibutylamino)coumarin, 3-(2-benzimidazoyl)-7-(diethylamino)coumarin, 3-(2-benzothiazoyl)-7-(dioctylamino)coumarin, 3-acetyl-7-(dimethylamino) coumarin, 3,3'-carbonylbis(7-dibutylamino)coumarin, 3,3'-carbonyl-7-diethylaminocoumarin-7'-bis(butoxyethyl) aminocoumarin, 10-[3-[4-(dimethylamino)phenyl]-1-oxo-2-propenyl]-2,3,6,7-1,1,7,7-tetramethyl1H, 5H,11H-[1] benzopyrano[6,7,8-ij]quinolizine-11-one, and 10-(2-benzothiazoyl)-2,3,6,7-tetrahydro-1,1,7,7-tetramethyl1H, 5H, 11H-[1]-benzopyrano[6,7,8-ij]quinolizin-11-one. Among these, 3,3'-carbonylbis(7-diethylaminocoumarin) and 3,3'-carbonylbis(7-dibutylaminocoumarin) are suitable.

Specific examples of the water-soluble acylphosphine oxides, thioxanthones or quaternary ammonium salts of thioxanthones, ketals, anthraquinones, benzoin alkyl ether compounds, and α-amino ketone compounds are those described in WO 2008/087977.

Among the examples mentioned above, a bisacylphosphine oxide represented by the formula (3) is particularly preferable because it allows the composition to have particularly excellent adhesive property.

Among the polymerization initiators (D) used in the present invention, a chemical polymerization initiator that is used preferably is organic peroxide. The organic peroxide used as the chemical polymerization initiator is not particularly limited and a known one can be used. Examples of typical organic peroxides include ketone peroxide, hydroperoxide, diacyl peroxide, dialkyl peroxide, peroxyketal, peroxyester, and peroxydicarbonate. Specific examples of these organic peroxides are those described in WO 2008/087977.

The amount of the polymerization initiator (D) to be added is not particularly limited. However, from the viewpoint of, for example, curability of the resultant composition, 0.001 to 20 parts by weight with respect to 100 parts by weight of the total amount of polymerizable monomers is preferable. When the amount of the polymerization initiator (D) to be added is less than 0.001 parts by weight, polymerization may not proceed sufficiently and bond strength may be reduced. Therefore, the amount is more preferably at least 0.01 parts by weight. On the other hand, when the amount of the polymerization initiator (D) to be added exceeds 20 parts by weight, in the case where the polymerization initiator itself has low polymerization performance, sufficiently high bond strength may not be obtained and further precipitation from the composition may occur. Therefore, the amount is more preferably 10 parts by weight or less and further preferably 5 parts by weight or less.

Next, optional components of the one-part dental adhesive composition of the present invention are described.

Polymerizable Monomer (E) Having One Polymerizable Group and at Least One Hydroxyl Group Preferably, the composition of the present invention includes the polymerizable monomer (E) having one polymerizable group and at least one hydroxyl group. Since the polymerizable monomer (E) has at least one hydroxyl group, it has good hydrophilicity. Accordingly, the polymerizable monomer (E) is a component that enhances the penetration effect and adhesive property of the composition and contributes also to the uniformity of the composition. Since the polymerizable monomer (E) has one polymerizable group, not only radical polymerization can occur but also copolymerization with another polymerizable monomer can occur. The polymerizable monomer (E) having one polymerizable group and at least one hydroxyl group is not particularly limited. The polymerizable group of the polymerizable monomer (E) is preferably a group that is radical-copolymerizable with a polymerizable group of the polymerizable monomer (A) and that of the polymerizable monomer (B). From the viewpoint of ease of radical polymerization, the polymerizable group of the polymerizable monomer (E) is preferably a (meth)acrylic group or (meth)acrylamide group. The polymerizable monomer (E) is used as a component of the dental adhesive composition. However, since the inside of an oral cavity has a humid environment, the polymerizable group may be detached by, for example, hydrolysis. When the stimulativeness of the detached polymerizable group to a biological body is taken into account, the polymerizable group of the polymerizable monomer (E) is preferably a methacrylic group or methacrylamide group.

The polymerizable monomer (E) can be used alone or two or more types thereof can be used in suitable combination. Examples of the polymerizable monomer (E) include 2-hydroxyethyl(meth)acrylate, 3-hydroxypropyl(meth)acrylate, 4-hydroxybutyl(meth)acrylate, 6-hydroxyhexyl(meth)acrylate, 10-hydroxydecyl(meth)acrylate, propylene glycol mono(meth)acrylate, glycerol mono(meth)acrylate, erythritol mono(meth)acrylate, N-methylol(meth)acrylamide, N-hydroxyethyl(meth)acrylamide, and N,N-(dihydroxyethyl)(meth)acrylamide. Among these, from the viewpoint of improving the penetrability into a collagen layer of dentin, 2-hydroxyethyl(meth)acrylate, 3-hydroxypropyl(meth)acrylate, glycerol mono(meth)acrylate, and erythritol mono(meth)acrylate are preferable and 2-hydroxyethylmethacrylate is particularly preferable.

The amount of the polymerizable monomer (E) to be added is not particularly limited. However, when the amount of the polymerizable monomer (E) to be added is too small, the effect of enhancing the penetration effect by the polymerizable monomer (E) may not be obtained, the uniformity of the composition may not be maintained, and the bond strength may be reduced. On the other hand, when the amount of the polymerizable monomer (E) to be added is too large, sufficiently high curability cannot be obtained and thus the mechanical strength of the cured product may be reduced. Therefore, preferably 10 to 50 parts by weight, more preferably 15 to 45 parts by weight of the polymerizable monomer (E) is contained in 100 parts by weight of the total amount of polymerizable monomers.

Polymerizable Monomer (F) Having Two Polymerizable Groups and Two Hydroxyl Groups Preferably, the composition of the present invention includes the polymerizable monomer (F) having two polymerizable groups and two hydroxyl groups represented by the general formula (2).

[Chemical Formula 6]

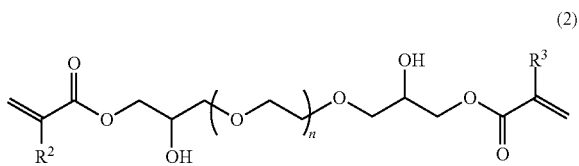

(2)

The polymerizable monomer (F) has crosslinkability because it has two polymerizable groups. The polymerizable monomer (F) has high hydrophilicity because it has two hydroxyl groups. Thus, the polymerizable monomer (F) is a component that increases the penetrability of the composition into a collagen layer of dentin, and at the same time it is a component that increases the mechanical strength of a resin-impregnated layer and enhances the bond durability. Furthermore, the polymerizable monomer (F) has an ethylene glycol unit as a spacer structure, and thus it can provide the cured product with proper flexibility. Therefore, it can be expected theoretically that even when occlusal load is applied repeatedly inside an oral cavity, no minute lost occurs in the adhesive layer and resin-impregnated layer, and the bond durability is enhanced and occurrence of a secondary caries due to bacterial entry is suppressed.

In the general formula (2), $R^2$ to $R^3$ each denote independently a hydrogen atom or a methyl group. From the viewpoint of stimulativeness to a biological body in the case where a polymerizable moiety is detached, a methyl group is preferable.

The number of the ethylene glycol unit is determined by the number n in the general formula (2). n denotes an integer of 1 to 5, and preferably n is an integer of 1 to 3. More preferably, n is 1 (that is, the polymerizable monomer (F) is 1,2-bis[3-(meth)acryloyloxy-2-hydroxypropoxy]ethane).

The polymerizable monomer (F) can be used alone or two or more types thereof can be used in combination.

The amount of the polymerizable monomer (F) to be added is not particularly limited. However, when the amount of the polymerizable monomer (F) to be added is too small, the effect of enhancing the penetration effect, mechanical strength and bond durability by the polymerizable monomer (F) may not be obtained. On the other hand, when the amount of the polymerizable monomer (F) to be added is too large, the decalcifying effect and penetration effect of the composition may be lowered and sufficient adhesive property may not be obtained. Therefore, the amount of the polymerizable monomer (F) to be added is preferably 5 to 20 parts by weight, and more preferably 5 to 15 parts by weight, in 100 parts by weight of the total amount of polymerizable monomers.

Crosslinkable Polymerizable Monomer (G)

Preferably, the composition of the present invention includes the crosslinkable polymerizable monomer (G) other than the polymerizable monomer (F) having two polymerizable groups and two hydroxyl groups represented by the general formula (2). The composition including the crosslinkable polymerizable monomer (G) has advantages such as a further enhanced bond strength.

The crosslinkable polymerizable monomer (G) can be used alone or two or more types thereof can be used in suitable combination. The crosslinkable polymerizable monomer (G) is not particularly limited. Examples thereof include an aromatic compound-based bifunctional polymerizable monomer, an aliphatic compound-based bifunctional polymerizable monomer, and trifunctional or higher polymerizable monomers. The term "bifunctional" indicates that the polymerizable monomer has two polymerizable groups, and the term "trifunctional" indicates that the polymerizable monomer has three polymerizable groups.

Examples of the aromatic compound-based bifunctional polymerizable monomer include 2,2-bis((meth)acryloyloxyphenyl)propane, 2,2-bis[4-(3-(meth)acryloyloxy)-2-hydroxypropoxyphenyl]propane (commonly known as "Bis-GMA"), 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, 2,2-bis(4-(meth)acryloyloxypentaethoxyphenynpropane, 2,2-bis(4-(meth)acryloyloxydipropoxyphenyl)propane, 2-(4-(meth)acryloyloxydiethoxyphenyl)-2-(4-(meth)acryloyloxyethoxyphenyl)-propane, 2-(4-(meth)acryloyloxydiethoxyphenyl)-2-(4-(meth)acryloyloxytriethoxy-phenyl)propane, 2-(4-(meth)acryloyloxydipropoxyphenyl)-2-(4-(meth)acryloyloxytriethoxy phenyl)propane, 2,2-bis(4-(meth)acryloyloxypropoxyphenyl)propane, 2,2-bis(4-(meth)

acryloyloxyisopropoxyphenyl)propane, and 1,4-bis(2-(meth)acryloyloxyethyl)pyromeritate.

Examples of the aliphatic compound-based bifunctional polymerizable monomer include glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, polyethylene glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, and 2,2,4-trimethylhexamethylenebis(2-carbamoyloxyethyl)dimethacrylate (commonly known as "UDMA").

Examples of the trifunctional or higher polymerizable monomers include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol tetra(meth)acrylate, dipentaerythritol penta(meth)acrylate, dipentaerythritol hexa(meth)acrylate, N,N-(2,2,4-trimethyl-hexamethylene)bis[2-(aminocarboxy)propane-1,3-diol]tetramethacrylate, and 1,7-diacryloyloxy-2,2,6,6-tetraacryloyloxymethyl-4-oxyheptane.

As the crosslinkable polymerizable monomer (G), 2,2-bis[4-(3-(meth)acryloyloxy)-2-hydroxypropoxyphenyl]propane, 2,2-bis(4-(meth)acryloyloxyethoxyphenyl)propane, 2,2-bis(4-(meth)acryloyloxypolyethoxyphenyl)propane, 2,2-bis(4-(meth)acryloyloxypropoxyphenyl)propane, 2,4-trimethylhexamethylenebis(2-carbamoyloxyethyl)dimethacrylate, triethylene glycol di(meth)acrylate, and glycerol di(meth)acrylate are preferable among the examples mentioned above, and 2,2-bis[4-(3-(meth)acryloyloxy)-2-hydroxypropoxyphenyl]propane, 2,4-trimethylhexamethylenebis(2-carbamoyloxyethyl)dimethacrylate, triethylene glycol di(meth)acrylate, and glycerol di(meth)acrylate are particularly preferable.

The amount of the crosslinkable polymerizable monomer (G) to be added is not particularly limited. However, when the amount of the polymerizable monomer (G) to be added is too small, the effect of enhancing the bond strength by the polymerizable monomer (G) may not be obtained. On the other hand, when the amount of the polymerizable monomer (G) to be added is too large, the penetration of the composition into a collagen layer of dentin becomes insufficient, which may result in that high bond strength is not obtained, and the uniformity of the composition may be impaired. Therefore, the amount of the polymerizable monomer (F) to be added is preferably 20 to 60 parts by weight, and more preferably 25 to 55 parts by weight, in 100 parts by weight of the total amount of polymerizable monomers.

Organic Solvent (H)

The composition of the present invention may contain the organic solvent (H) in order to enhance the solubility of the polymerizable monomers and thus obtain a uniform composition. The organic solvent (H) can be used alone or two or more types thereof can be used in suitable combination. Examples of the organic solvent (H) include methanol, ethanol, 1-propanol, 2-propanol, 1-butanol, 2-methyl-2-propanol, acetone, methyl ethyl ketone, tetrahydrofuran, diethyl ether, diisopropyl ether, hexane, toluene, chloroform, ethyl acetate, and butyl acetate. Particularly, when both safety to biological bodies and easy removal based on volatility are taken into consideration, the organic solvent (H) is preferably a water-soluble organic solvent. Specifically, ethanol, 2-propanol, 2-methyl-2-propanol, acetone, and tetrahydrofuran can be used preferably. The amount of the organic solvent (H) to be added is not particularly limited. Preferably, it is 1 to 1000 parts by weight, and more preferably 5 to 200 parts by weight, with respect to 100 parts by weight of the total amount of polymerizable monomers.

Polymerization Accelerator (I)

In an preferred embodiment, the polymerization accelerator (I) is used. Examples of the polymerization accelerator (I) used in the present invention include amines, sulfinic acids and salts thereof, borate compounds, barbituric acid derivatives, triazine compounds, copper compounds, tin compounds, vanadium compounds, halogen compounds, aldehydes, thiol compounds, sulfite, bisulfite, and thiourea compounds.

Amines used as the polymerization accelerator (I) can be divided into aliphatic amines and aromatic amines. Examples of the aliphatic amines include: primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. Among these, tertiary aliphatic amines are preferable from the viewpoint of curability and storage stability of the composition, and particularly, N-methyldiethanolamine and triethanolamine are used more preferably.

Examples of the aromatic amine include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, and N,N-dimethyl-3,5-di-t-butylaniline, 4-N,N-dimethylaminobenzoic acid ethyl ester, 4-N,N-dimethylaminobenzoic acid methyl ester, 4-N,N-dimethylaminobenzoic acid n-butoxyethyl ester, 4-N,N-dimethylaminobenzoic acid 2-(methacryloyloxy)ethyl ester, 4-N,N-dimethylaminobenzophenone, and 4-N,N-dimethylaminobenzoic acid butyl ester. Among these, at least one selected from the group consisting of N,N-di(2-hydroxyethyl)-p-toluidine, 4-N,N-dimethylaminobenzoic acid ethyl ester, 4-N,N-dimethylaminobenzoic acid n-butoxyethyl ester, and 4-N,N-dimethylaminobenzophenone is used preferably from the viewpoint of being capable of providing the composition with excellent curability.

Specific examples of the sulfinic acids and salts thereof, borate compounds, barbituric acid derivatives, triazine compounds, copper compounds, tin compounds, vanadium compounds, halogen compounds, aldehydes, thiol compounds, sulfite, bisulfite, and thiourea compounds are those described in WO 2008/087977.

The amount of the polymerization accelerator (I) to be added in the present invention is not particularly limited. However, from the viewpoints of, for example, curability of the resultant composition, it is preferable that 0.001 to 30 parts by weight of the polymerization accelerator (I) is contained with respect to 100 parts by weight of the total amount of polymerizable monomers. When the amount of the polymerization accelerator (I) to be added is less than 0.001 parts by weight, polymerization may not proceed sufficiently and bond strength may be reduced. Therefore, the amount is more preferably at least 0.05 part by weight. On the other hand, when the amount of the polymerization accelerator (I) to be added exceeds 30 parts by weight, in the case where the polymerization initiator itself has low polymerization performance, sufficiently high bond strength may not be obtained and further precipitation from the composition may occur. Therefore, the amount is more preferably 20 parts by weight or less.

Filler (J)

The composition of the present invention may include the filler (J). Generally, such fillers are divided roughly into organic fillers, inorganic fillers, and organic-inorganic composite fillers. Examples of materials for the organic fillers include polymethylmethacrylate, polyethylmethacrylate, a methylmethacrylate-ethylmethacrylate copolymer, cross-linked polymethylmethacrylate, cross-linked polyethylmethacrylate, polyamide, polyvinyl chloride, polystyrene, chloroprene rubber, nitrile rubber, an ethylene-vinyl acetate copolymer, a styrene-butadiene copolymer, an acrylonitrile-styrene copolymer, and an acrylonitrile-styrene-butadiene copolymer. These may be used alone or a mixture of two or more of them may be used. The shapes of the organic fillers are not particularly limited, and particle sizes of the fillers to be used can be selected appropriately. From the viewpoints of, for example, handleability and mechanical strength of the resultant composition, the mean particle size of the organic fillers is preferably 0.001 to 50 µm and more preferably 0.001 to 10 µm.

Examples of materials for the inorganic fillers include quartz, silica, alumina, silica-titania, silica-titania-barium oxide, silica-zirconia, silica-alumina, lanthanum glass, borosilicate glass, soda glass, barium glass, strontium glass, glass ceramics, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontiumcalcium fluoroaluminosilicate glass. Similarly, these can be used alone or two or more of them can be used in mixture. The shapes of the inorganic fillers are not particularly limited and particle sizes of the fillers to be used can be selected suitably. From the viewpoints of, for example, handleability and mechanical strength of the resultant composition, the mean particle size of the inorganic fillers is preferably 0.001 to 50 µm and more preferably 0.001 to 10 µm.

Examples of the shapes of the inorganic fillers include amorphous fillers and spherical fillers. From the viewpoint of improving the mechanical strength of the composition, it is preferable that spherical fillers are used as the inorganic fillers. In this case, the spherical fillers are fillers in which when a photograph thereof is taken with a scanning electron microscope (hereinafter abbreviated as SEM), particles observed within a unit field of view are rounded and the mean uniformity obtained by dividing the particle size in the direction orthogonal to the maximum diameter by the maximum diameter is at least 0.6. The mean particle size of the spherical fillers is preferably 0.001 to 5 µm. When the mean particle size is less than 0.001 µm, the filling rate of the spherical fillers in the composition decreases and thereby the mechanical strength may be reduced. On the other hand, when the mean particle size exceeds 5 µm, the surface areas of the spherical fillers are reduced and a cured body with high mechanical strength may not be obtained.

The inorganic fillers may be used after the surfaces thereof are treated beforehand with a known surface-treating agent such as a silane coupling agent in order to adjust fluidity of the composition as required. Examples of such a surface-treating agent include vinyltrimethoxysilane, vinyltriethoxysilane, vinyltrichlorosilane, vinyltri(β-methoxyethoxy)silane, γ-methacryloyloxypropyltrimethoxysilane, 11-methacryloyloxyundecyltrimethoxysilane, γ-glycidoxypropyltrimethoxysilane, γ-mercaptopropyltrimethoxysilane, and γ-aminopropyltriethoxysilane.

The organic-inorganic composite filler used in the present invention can be obtained as follows. That is, a monomer compound is added to the aforementioned inorganic filler beforehand, this is made into a paste and is then polymerized, and thereafter this is crushed. The organic-inorganic composite filler that can be used is, for example, a TMPT filler (obtained by mixing trimethylolpropane methacrylate with a silica filler, polymerizing it, and then crushing it). The shape of the organic-inorganic composite filler is not particularly limited, and the particle size of the filler to be used can be selected appropriately. From the viewpoints of, for example, handleability and mechanical strength of the resultant composition, the mean particle size of the organic-inorganic composite filler is preferably 0.001 to 50 µm and more preferably 0.001 to 10 µm.

As the filler (J), an inorganic filler having a primary particle diameter of 0.001 to 5 µm is preferable, and a silica filler having a primary particle diameter of 0.001 to 0.1 µm is more preferable.

The amount of the filler (J) to be added in the present invention is not particularly limited. Preferably, it is 1 to 100 parts by weight, more preferably 3 to 50 parts by weight, with respect to 100 parts by weight of the total amount of polymerizable monomers.

In the present invention, the phrase "the respective components of the one-part dental adhesive composition have been mixed uniformly" indicates a state in which the polymerizable monomers, the solvent, the polymerization initiator and the polymerization accelerator included in the composition are mutually dissolved with each other at 25° C. In the case where the filler (J) is added, the phrase indicates a state in which they are mutually dissolved with each other at 25° C., and furthermore the filler (J) is dispersed in the one-part dental adhesive without being separated and sedimented.

Fluorine Ion-Releasing Material

The composition of the present invention further may include a fluorine ion-releasing material. Addition of the fluorine ion-releasing material makes it possible to obtain a composition capable of providing the tooth structure with acid resistance. Examples of the fluorine ion-releasing material include metal fluorides such as sodium fluoride, potassium fluoride, sodium monofluorophosphate, lithium fluoride and ytterbium fluoride.

In addition, for example, a pH adjuster, polymerization inhibitor, ultraviolet absorbent, thickening agent, colorant, antibacterial agent, and flavor may be added to the composition of the present invention within a range that does not inhibit the effect of the present invention.

The dental adhesive composition of the present invention is one-part type and the composition can be accommodated in one container. The one-part dental adhesive composition of the present invention can be produced by mixing the respective components according to a known method.

The one-part dental adhesive composition of the present invention can be used when, for example, bonding a dental restorative material, such as a dental composite resin, a dental compomer and a dental resin cement, to a tooth structure.

In this case, the one-part dental adhesive composition of the present invention can be used as a one-step adhesive. That is, it is possible to apply the one-part dental adhesive composition of the present invention directly to a tooth structure without using a pretreatment agent such as an etching material, a primer and a self-etching primer.

The one-part dental adhesive composition of the present invention has high stability to ambient light, and makes it possible to ensure sufficiently the working time and the tooth structure treatment time necessary for the decalcifying and penetration effects. Moreover, the one-part dental adhesive composition of the present invention exhibits excellent adhesive property and bond durability to a tooth structure (particularly dentin). Furthermore, since the respective components have been mixed uniformly in the one-part dental adhesive composition of the present invention, the work of mixing uniformly the respective components at the time of use is unnecessary. Therefore, the dental composition of the present invention can be used easily. In addition, a cured product of the one-part dental adhesive composition of the present invention has low water absorptivity and high coloration resistance.

EXAMPLES

Hereinafter, the present invention is described in detail with reference to Examples and Comparative Examples, but the present invention is not limited to the Examples. Abbreviated names and words used below are as follows.
MDP: 10-methacryloyloxydecyl dihydrogen phosphate
4-META: 4-methacryloyloxyethyl trimellitate
6-MHPA: 6-methacryloyloxyhexyl phosphonoacetate
HEMA: 2-hydroxyethylmethacrylate
4FMA: tetrafluoropropyl methacrylate

[Chemical Formula 7]

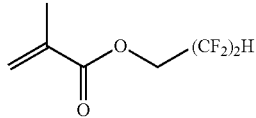

8FMA: octafluoropentyl methacrylate

[Chemical Formula 8]

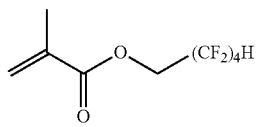

DPEPA19F:

[Chemical Formula 9]

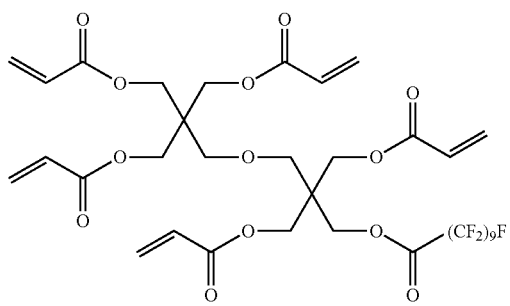

GEDMA: 1,2-bis(3-methacryloyloxy-2-hydroxypropoxy) ethane

Bis-GMA: 2,2-bis[4-(3-methacryloyloxy)-2-hydroxypropoxyphenyl]propane
UDMA: 2,2,4-trimethylhexamethylenebis(2-carbamoyloxyethyl)dimethacrylate
TEGDMA: triethyleneglycol dimethacrylate
GDMA: glycerol dimethacrylate
TMDPO: 2,4,6-trimethylbenzoyldiphenylphosphine oxide
BAPO: bis(2,4,6-trimethylbenzoyl)phenylphosphine oxide
CQ: camphorquinone
PDE: ethyl p-(N,N-dimethylamino)benzoate
DEPT: N,N-di(2-hydroxyethyl)-p-toluidine
TTA: triethanolamine
Inorganic filler 1: "R972" manufactured by Japan Aerosil Inc.

(1) Production of One-Part Dental Adhesive Composition

The respective components listed in Tables 1 to 3 were mixed together at an ordinary temperature and thereby one-part dental adhesive compositions were produced. On these compositions, adhesive property test (1), adhesive property test (2), uniformity evaluation, water absorption test, coloration resistance test, and test of sensitivity to ambient light were conducted according to the after-mentioned method. Tables 1 to 3 show the compositions and evaluation results.

Adhesive Property Test (1)

The labial surface of a bovine mandibular incisor was ground with #80 silicon carbide paper (manufactured by Nihon Kenshi Co., Ltd.) under running water, and thereby a sample with an exposed flat surface of dentin was obtained. The sample thus obtained further was ground with #1000 silicon carbide paper (manufactured by Nihon Kenshi Co., Ltd.) under running water. After completion of grinding, water on the surface was air-blown to be dried. An adhesive tape with a thickness of about 150 μm having a circular hole whose diameter was 3 mm was attached to the smooth surface that had been dried and thereby the adhesive area was defined.

Each one-part adhesive produced above was applied into the above-mentioned circular hole using a brush and was then allowed to stand for 10 seconds. Thereafter, the surface thereof was air-blown and thereby the one-part adhesive thus applied was dried until it lost fluidity. Subsequently, it was irradiated with light using a dental visible light unit "JET LITE 3000" (manufactured by J. Morita USA) for 10 seconds. Thus, the one-part adhesive that had been applied was cured.

A composite resin for dental filling (trade name "Clearfil AP-X" (registered trademark), produced by Kuraray Medical Inc.) was applied on a surface of the cured body of the one-part adhesive thus formed, and covered with a mold releasing film (made of polyester). Next, slide glass was placed on the mold release film to press it, and thereby the surface of the applied composite resin was smoothed. Subsequently, the composite resin was irradiated with light for 20 seconds using the aforementioned light unit "JET LITE 3000" through the mold release film. Thus, the composite resin was cured.

One end face (circular section) of a stainless-steel cylindrical rod (with a diameter of 7 mm and a length of 2.5 cm) was bonded to the surface of the resultant cured product of the dental filling composite resin using a commercially available dental resin cement (manufactured by Kuraray Medical Inc., "PANAVIA21" (trade name)). After bonding, this sample was allowed to stand still at room temperature for 30 minutes and was then immersed in distilled water. Ten adhesive property test samples were produced in total, and allowed to stand still for 24 hours inside a thermostat whose temperature was maintained at 37° C. With respect to five samples out of the ten samples, in order to evaluate the adhesivity in the early bonding stage, the bond strength was measured immediately after they were allowed to stand still for 24 hours. With respect to the other five samples, in order to evaluate bond durability, the bond strength was measured after 4000 thermal cycles had been performed, with one cycle being a process for further immersing each sample in 4° C. cold water and 60° C. warm water alternately for one minute.

The tensile bond strengths of the above-mentioned adhesive property test samples were measured with a universal testing machine (manufactured by Shimadzu Corporation), with the crosshead speed being set at 2 mm/min, and the average value thereof was taken as tensile bond strength.

Adhesive Property Test (2)

The center of a human third molar crown portion was cut perpendicularly to the tooth axis by using a low-speed precision saw "IsoMet 5000" (manufactured by Buehler), and thereby a sample with an exposed flat surface of dentin was obtained. The sample thus obtained was ground with #600 silicon carbide paper (produced by Nihon Kenshi Co., Ltd.) under running water.

After completion of grinding, water on the surface of the sample was air-blown to dry the sample, and each one-part adhesive produced above was applied thereto using a brush and allowed to stand for 10 seconds. Thereafter, the surface thereof was air-blown and thereby the one-part adhesive thus applied was dried until it lost fluidity. Subsequently, it was irradiated with light using the dental visible light unit "JET LITE 3000" (manufactured by J. Morita USA) for 10 seconds. Thus, the one-part adhesive applied was cured.

A composite resin for dental filling (trade name "Clearfil AP-X" (registered trademark), produced by Kuraray Medical Inc.) was mounded in a thickness of 1 mm on a surface of the cured body of the one-part adhesive thus formed, and irradiated with light using the light unit "JET LITE 3000" for 20 seconds. Thus, the composite resin was cured. The composite resin was applied further thereon in a thickness of 2 mm and irradiated with light, which was repeated two times so that the composite resin had a total thickness of 5 mm. Then the sample was immersed in distilled water.

Two adhesive property test samples were produced in total, and allowed to stand still for 24 hours inside a thermostat whose temperature was maintained at 37° C. A specimen was cut out from one of the samples and measured for bond strength immediately after the sample was allowed to stand still for 24 hours, in order to evaluate the adhesivity in the early bonding stage. The other sample was embedded in an epoxy resin in a brass cup, and then a load of 8 kg was applied thereto 100,000 times using a Leinfelder tester, in order to evaluate the bond durability. After the load was applied, the sample was taken out from the cup and a specimen was cut out therefrom to be measured for bond strength.

Each specimen was cut out, in the longitudinal direction, as a slice with a thickness of 1.0 mm under running water using the low-speed precision saw "IsoMet 5000". Subsequently, the slice was cut into pieces with a width of 1.0 mm so that each piece has an adhesion area of 1 mm². Thus, 10 to 20 stick-like specimens were produced.

Each stick-like specimen thus obtained was fixed to a jig with a repairing agent for models "Model Repair II Blue" (sold by Dentsply Sankin), and measured for bond strength using a compact table-top tester "EZ Test" (manufactured by Shimadzu Corp.), with the crosshead speed being set at 1 mm/min. The average value of the stick-like specimens was defined as micro-tensile bond strength.

Uniformity Evaluation

The respective components were mixed at an ordinary temperature, and then the mixtures were allowed to stand still at 25° C. for 10 minutes. The mixtures each were evaluated visually to see whether the respective components of the one-part dental adhesive were dispersed uniformly without being separated and sedimented. They were evaluated as being uniform when the polymerizable monomers, the solvent, the polymerization initiator and the polymerization accelerator included in the one-part dental adhesive were mutually dissolved with each other, and the filler, if added, was dispersed in the one-part dental adhesive without being separated and sedimented.

Water Absorption Test

Each one-part adhesive was air-blown, and the water and organic solvent were removed until the weight stopped changing. Thus, a sample for producing a cured product was obtained. The obtained sample was put in a Teflon (registered trademark) mold (with a diameter of 10 mm and a thickness of 1 mm) placed on a slide glass on which a polyester film was laid. A polyester film was placed on top of it, and further a glass sheet was pressed against it lightly. This was irradiated with light from the top using the light unit "JET LITE 3000" for 10 seconds, and then it was turned over and irradiated with light in the same manner for 10 seconds to cure the sample. Thus, a cured product of each one-part adhesive was obtained.

The unpolymerized portion of the obtained cured product was wiped off and the cured product was immersed in water in a thermostat at 37° C. for 24 hours. The cured product was taken out and water was wiped off, and the cured product was measured for weight (weight A). Subsequently, the cured product was dried in a thermostat at 90° C. for 3 hours, and then cooled to a room temperature in a desiccator holding silica gel, and the cured product was measured for weight (weight B). The water absorption rate of the cured product was calculated by the following formula.

$$\text{Water absorption rate} = (\text{weight } A - \text{weight } B) \div \text{weight } B \times 100 \, (\%)$$

Coloration Resistance Test

Turmeric (0.005 g) [produced by Gaban Co., Ltd.] was put into distilled water (100 mL) to prepare an yellow turmeric suspension. A cured product of each one-part adhesive produced by the same method as in the water absorption test was immersed in the suspension. It was kept in a thermostat at 37° C. for 18 hours, and then the cured product was taken out and washed with running water for 1 minute.

Thereafter, the cured product was observed visually to see the degree of coloration.

Test of Sensitivity to Ambient Light

One drop (about 20 mg) of each one-part adhesive was taken on a mixing saucer and allowed to stand for a specified period of time under dental light adjusted to an illuminance of 8,000 luxes. Then, the sample was dipped up with a brush and checked for presence of a gelatinous substance. The measurements were made at an interval of 10 seconds, and the longest period of time during which no gelatinous substance was observed was defined as the working time.

TABLE 1

| Components | | Example 1 | Example 2 | Example 3 | Example 4 | Example 5 | Example 6 |
|---|---|---|---|---|---|---|---|
| Polymerizable monomer (A) having an acidic group | MDP | 15 | 15 | 15 | 15 | 15 | 15 |
| Polymerizable monomer (B) having a fluorocarbon group | 4FMA | 2 | | | | | |
| | 8FMA | | 0.5 | 2 | 5 | 10 | 15 |
| | DPEPA19F | | | | | | |
| Polymerizable monomer (E) having one polymerizable group and at least one hydroxyl group | HEMA | 42 | 42.5 | 42 | 40 | 38 | 35 |
| Crosslinkable polymerizable monomer (G) | Bis-GMA | 41 | 42 | 41 | 40 | 37 | 35 |
| Water (C) | Distilled water | 20 | 20 | 20 | 20 | 20 | 20 |
| Organic solvent (H) | Ethanol | 20 | 20 | 20 | 20 | 20 | 20 |
| Polymerization initiator (D) | TMDPO | 5 | 5 | 5 | 5 | 5 | 5 |
| Polymerization accelerator (I) | DEPT | 2 | 2 | 2 | 2 | 2 | 2 |
| Filler (J) | Inorganic filler 1 | 10 | 10 | 10 | 10 | 10 | 10 |
| Bond strength to dentin (MPa) | After 24 hours | 17.5 | 17.3 | 18.6 | 17.9 | 17.0 | 15.3 |
| | After thermal cycles | 16.5 | 16.4 | 18.5 | 17.5 | 16.7 | 15.0 |
| Micro-tensile bond strength to dentin (MPa) | After 24 hours | 52.1 | 51.9 | 53.2 | 52.5 | 49.7 | 45.4 |
| | After load applied | 47.8 | 48.2 | 49.6 | 46.4 | 44.8 | 40.3 |
| Uniformity | | Uniform | Uniform | Uniform | Uniform | Uniform | Uniform |
| Water absorption ratio of bond cured product (%) | | 8.8 | 8.8 | 8.4 | 8.1 | 7.4 | 7.2 |
| Coloration of bond cured product | | Light yellow | Light yellow | Light yellow | Light yellow | No coloration | No coloration |
| Sensitivity to ambient light | | 60 seconds | 60 seconds | 60 seconds | 60 seconds | 70 seconds | 70 seconds |

| Components | | Example 7 | Example 8 | Example 9 | Example 10 | Example 11 | C. Example 1 |
|---|---|---|---|---|---|---|---|
| Polymerizable monomer (A) having an acidic group | MDP | 10 | 20 | 30 | 15 | 15 | 15 |
| Polymerizable monomer (B) having a fluorocarbon group | 4FMA | | | | | | |
| | 8FMA | 2 | 2 | 2 | 2 | 2 | |
| | DPEPA19F | | | | | | |
| Polymerizable monomer (E) having one polymerizable group and at least one hydroxyl group | HEMA | 44 | 37 | 28 | 42 | 42 | 43 |
| Crosslinkable polymerizable monomer (G) | Bis-GMA | 44 | 41 | 40 | 41 | 41 | 42 |
| Water (C) | Distilled water | 20 | 20 | 20 | 20 | 20 | 20 |
| Organic solvent (H) | Ethanol | 20 | 20 | 20 | 20 | | 20 |
| Polymerization initiator (D) | TMDPO | 5 | 5 | 5 | 5 | 5 | 5 |
| Polymerization accelerator (I) | DEPT | 2 | 2 | 2 | 2 | 2 | 2 |
| Filler (J) | Inorganic filler 1 | 10 | 10 | 10 | 10 | 10 | 10 |
| Bond strength to dentin (MPa) | After 24 hours | 18.2 | 18.5 | 16.0 | 17.2 | 16.2 | 16.9 |
| | After thermal cycles | 18.4 | 18.1 | 15.4 | 16.8 | 15.9 | 14.1 |
| Micro-tensile bond strength to dentin (MPa) | After 24 hours | 50.3 | 51.6 | 48.3 | 50.8 | 48.3 | 47.9 |
| | After load applied | 45.8 | 47.3 | 44.8 | 45.9 | 44.8 | 42.2 |
| Uniformity | | Uniform | Uniform | Uniform | Uniform | Uniform | Uniform |
| Water absorption ratio of bond cured product (%) | | 8.2 | 9.0 | 9.8 | 8.3 | 8.8 | 12.5 |
| Coloration of bond cured product | | No coloration | Light yellow | Light yellow | Light yellow | Light yellow | Yellow |
| Sensitivity to ambient light | | 50 seconds | 60 seconds | 60 seconds | 50 seconds | 50 seconds | 60 seconds |

| Components | | C. Example 2 | C. Example 3 | C. Example 4 | C. Example 5 |
|---|---|---|---|---|---|
| Polymerizable monomer (A) having an acidic group | MDP | 15 | 2 | 40 | 15 |
| Polymerizable monomer (B) having a fluorocarbon group | 4FMA | | | | |
| | 8FMA | 2 | 2 | 2 | |
| | DPEPA19F | | | | 20 |
| Polymerizable monomer (E) having one polymerizable group and at least one hydroxyl group | HEMA | 42 | 48 | 17 | 33 |
| Crosslinkable polymerizable monomer (G) | Bis-GMA | 41 | 48 | 41 | 32 |
| Water (C) | Distilled water | | 20 | 20 | 20 |
| Organic solvent (H) | Ethanol | | 20 | 20 | 20 |
| Polymerization initiator (D) | TMDPO | 5 | 5 | 5 | 5 |
| Polymerization accelerator (I) | DEPT | 2 | 2 | 2 | 2 |

TABLE 1-continued

| | | | | | |
|---|---|---|---|---|---|
| Filler (J) | Inorganic filler 1 | 10 | 10 | 10 | 10 |
| Bond strength to dentin (MPa) | After 24 hours | 10.1 | 13.3 | 12.3 | 13.8 |
| | After thermal cycles | 4.6 | 13.0 | 10.0 | 13.6 |
| Micro-tensile bond strength to dentin (MPa) | After 24 hours | 28.2 | 34.4 | 31.8 | 32.7 |
| | After load applied | 23.6 | 29.1 | 18.9 | 28.4 |
| Uniformity | | Uniform | Uniform | Nonuniform | Nonuniform |
| Water absorption ratio of bond cured product (%) | | 8.6 | 7.2 | 20.1 | 5.5 |
| Coloration of bond cured product | | Light yellow | No coloration | Yellow | No coloration |
| Sensitivity to ambient light | | 20 seconds | 40 seconds | 70 seconds | 30 seconds |

*The amounts of respective components added are indicated in the unit of parts by weight.

TABLE 2

| Components | | Example 12 | Example 13 | Example 14 | Example 15 | Example 16 |
|---|---|---|---|---|---|---|
| Polymerizable monomer (A) having an acidic group | MDP | | | 15 | 15 | 15 |
| | 4-META | 15 | | | | |
| | 6-MHPA | | 15 | | | |
| Polymerizable monomer (B) having a fluorocarbon group | 4FMA | | | | | |
| | 8FMA | 2 | 2 | 2 | 2 | 2 |
| Polymerizable monomer (E) having one polymerizable group and at least one hydroxyl group | HEMA | 42 | 42 | | | 42 |
| Polymerizable monomer (F) having two polymerizable groups and two hydroxyl groups | GEDMA | | | | | |
| Crosslinkable polymerizable monomer (G) | Bis-GMA | 41 | 41 | 41 | 41 | |
| | UDMA | | | | | 41 |
| | TEGDMA | | | 42 | | |
| | GDMA | | | | 42 | |
| Water (C) | Distilled water | 20 | 20 | 15 | 15 | 20 |
| Organic solvent (H) | Ethanol | 20 | 20 | 40 | 40 | 20 |
| Polymerization initiator (D) | TMDPO | 5 | 5 | 5 | 5 | 5 |
| | BAPO | | | | | |
| | CQ | | | | | |
| Polymerization accelerator (I) | PDE | | | | | |
| | DEPT | 2 | 2 | 2 | 2 | 2 |
| | TTA | | | | | |
| Fluorine ion-releasing component | Sodium fluoride | | | | | |
| Filler (J) | Inorganic filler 1 | 10 | 10 | 10 | 10 | 10 |
| Bond strength to dentin (MPa) | After 24 hours | 15.4 | 17.2 | 15.0 | 15.3 | 18.7 |
| | After thermal cycles | 15.9 | 16.6 | 15.1 | 15.1 | 18.6 |
| Micro-tensile bond strength to dentin (MPa) | After 24 hours | 45.7 | 47.3 | — | — | 52.1 |
| | After load applied | 41.8 | 43.6 | — | — | 48.6 |
| Uniformity | | Uniform | Uniform | Uniform | Uniform | Uniform |
| Water absorption ratio of bond cured product (%) | | 8.6 | 8.5 | 6.1 | 6.0 | 8.2 |
| Coloration of bond cured product | | Light yellow | Light yellow | No coloration | No coloration | Light yellow |
| Sensitivity to ambient light | | 60 seconds | 60 seconds | 60 seconds | 60 seconds | 60 seconds |

| Components | | Example 17 | Example 18 | Example 19 | Example 20 | Example 21 |
|---|---|---|---|---|---|---|
| Polymerizable monomer (A) having an acidic group | MDP | 15 | 15 | 15 | 15 | 15 |
| | 4-META | | | | | |
| | 6-MHPA | | | | | |
| Polymerizable monomer (B) having a fluorocarbon group | 4FMA | | | | | |
| | 8FMA | 2 | 2 | 2 | 2 | 2 |
| Polymerizable monomer (E) having one polymerizable group and at least one hydroxyl group | HEMA | 42 | 32 | 32 | 32 | 32 |
| Polymerizable monomer (F) having two polymerizable groups and two hydroxyl groups | GEDMA | | | 10 | 10 | 10 | 10 |
| Crosslinkable polymerizable monomer (G) | Bis-GMA | 41 | 41 | 41 | 41 | 41 |
| | UDMA | | | | | |
| | TEGDMA | | | | | |
| | GDMA | | | | | |
| Water (C) | Distilled water | 20 | 20 | 20 | 20 | 20 |
| Organic solvent (H) | Ethanol | 20 | 20 | 20 | 20 | 20 |

TABLE 2-continued

| | | | | | | |
|---|---|---|---|---|---|---|
| Polymerization initiator (D) | TMDPO | 5 | 5 | | | |
| | BAPO | | | 2 | 2 | 2 |
| | CQ | | | | 2 | 2 |
| Polymerization accelerator (I) | PDE | | | | 2 | 2 |
| | DEPT | | 2 | 2 | 2 | 2 |
| | TTA | 2 | | | | |
| Fluorine ion-releasing component | Sodium fluoride | | | | | 0.1 |
| Filler (J) | Inorganic filler 1 | 10 | 10 | 10 | 10 | 10 |
| Bond strength to dentin (MPa) | After 24 hours | 19.2 | 19.0 | 19.3 | 20.1 | 19.8 |
| | After thermal cycles | 19.1 | 19.4 | 19.6 | 20.3 | 19.7 |
| Micro-tensile bond strength to dentin (MPa) | After 24 hours | 56.2 | 58.7 | 59.3 | 63.4 | 62.8 |
| | After load applied | 50.9 | 57.3 | 59.2 | 61.8 | 62.2 |
| Uniformity | | Uniform | Uniform | Uniform | Uniform | Uniform |
| Water absorption ratio of bond cured product (%) | | 8.6 | 7.3 | 7.3 | 7.0 | 6.8 |
| Coloration of bond cured product | | Light yellow | No coloration | No coloration | No coloration | No coloration |
| Sensitivity to ambient light | | 60 seconds | 50 seconds | 50 seconds | 50 seconds | 50 seconds |

*The amounts of respective components added are indicated in the unit of parts by weight.

TABLE 3

| Components | | Example 22 | Example 23 | Example 24 | Example 25 | Example 26 | Example 27 |
|---|---|---|---|---|---|---|---|
| Polymerizable monomer (A) having an acidic group | MDP | 15 | 15 | 15 | 10 | 20 | 30 |
| Polymerizable monomer (B) having a fluorocarbon group | 8FMA | 0.5 | 5 | 10 | 2 | 2 | 2 |
| Polymerizable monomer (E) having one polymerizable group and at least one hydroxyl group | HEMA | 32.5 | 30 | 28 | 34 | 27 | 18 |
| Polymerizable monomer (F) having two polymerizable groups and two hydroxyl groups | GEDMA | 10 | 10 | 10 | 10 | 10 | 10 |
| Crosslinkable polymerizable monomer (G) | Bis-GMA | 42 | 40 | 37 | 44 | 41 | 40 |
| Water (C) | Distilled water | 20 | 20 | 20 | 20 | 20 | 20 |
| Organic solvent (H) | Ethanol | 20 | 20 | 20 | 20 | 20 | 20 |
| Polymerization initiator (D) | TMDPO | 5 | 5 | 5 | 5 | 5 | 5 |
| | BAPO | | | | | | |
| | CQ | | | | | | |
| Polymerization accelerator (I) | PDE | | | | | | |
| | DEPT | 2 | 2 | 2 | 2 | 2 | 2 |
| | TTA | | | | | | |
| Filler (J) | Inorganic filler 1 | 10 | 10 | 10 | 10 | 10 | 10 |
| Bond strength to dentin (MPa) | After 24 hours | 19.3 | 18.3 | 17.7 | 18.7 | 18.9 | 16.7 |
| | After thermal cycles | 19.0 | 18.1 | 17.3 | 19.1 | 18.8 | 16.0 |
| Micro-tensile bond strength to dentin (MPa) | After 24 hours | 56.5 | 53.4 | 52.3 | 53.5 | 54.7 | 51.6 |
| | After load applied | 56.3 | 52.8 | 51.9 | 52.4 | 53.1 | 50.9 |
| Uniformity | | Uniform | Uniform | Uniform | Uniform | Uniform | Uniform |
| Water absorption ratio of bond cured product (%) | | 7.5 | 6.8 | 6.1 | 6.9 | 7.7 | 8.5 |
| Coloration of bond cured product | | Light yellow | Light yellow | No coloration | No coloration | Light yellow | Light yellow |
| Sensitivity to ambient light | | 60 seconds | 50 seconds | 60 seconds | 50 seconds | 50 seconds | 50 seconds |

| Components | | Example 28 | Example 29 | Example 30 | Example 31 | Example 32 | Example 33 |
|---|---|---|---|---|---|---|---|
| Polymerizable monomer (A) having an acidic group | MDP | 15 | 15 | 15 | 15 | 10 | 20 |
| Polymerizable monomer (B) having a fluorocarbon group | 8FMA | 2 | 0.5 | 5 | 10 | 2 | 2 |
| Polymerizable monomer (E) having one polymerizable group and at least one hydroxyl group | HEMA | 32 | 32.5 | 30 | 28 | 34 | 27 |
| Polymerizable monomer (F) having two polymerizable groups and two hydroxyl groups | GEDMA | 10 | 10 | 10 | 10 | 10 | 10 |
| Crosslinkable polymerizable monomer (G) | Bis-GMA | 41 | 42 | 40 | 37 | 44 | 41 |
| Water (C) | Distilled water | 20 | 20 | 20 | 20 | 20 | 20 |
| Organic solvent (H) | Ethanol | 20 | 20 | 20 | 20 | 20 | 20 |

TABLE 3-continued

| | | | | | | | |
|---|---|---|---|---|---|---|---|
| Polymerization initiator (D) | TMDPO | 5 | | | | | |
| | BAPO | | 2 | 2 | 2 | 2 | 2 |
| | CQ | | 2 | 2 | 2 | 2 | 2 |
| Polymerization accelerator (I) | PDE | | 2 | 2 | 2 | 2 | 2 |
| | DEPT | | 2 | 2 | 2 | 2 | 2 |
| | TTA | 2 | | | | | |
| Filler (J) | Inorganic filler 1 | 10 | 10 | 10 | 10 | 10 | 10 |
| Bond strength to dentin (MPa) | After 24 hours | 17.0 | 19.5 | 18.5 | 17.9 | 18.9 | 19.1 |
| | After thermal cycles | 16.5 | 19.2 | 18.3 | 17.5 | 19.3 | 19.0 |
| Micro-tensile bond strength to dentin (MPa) | After 24 hours | 52.3 | 57.5 | 54.4 | 53.3 | 54.5 | 54.8 |
| | After load applied | 51.8 | 56.7 | 53.9 | 52.9 | 53.4 | 53.1 |
| Uniformity | | Uniform | Uniform | Uniform | Uniform | Uniform | Uniform |
| Water absorption ratio of bond cured product (%) | | 7.1 | 7.1 | 6.5 | 5.7 | 6.5 | 7.4 |
| Coloration of bond cured product | | Light yellow | Light yellow | Light yellow | No coloration | No coloration | Light yellow |
| Sensitivity to ambient light | | 50 seconds | 50 seconds | 50 seconds | 50 seconds | 50 seconds | 50 seconds |

| | Components | | Example 34 | Example 35 | Example 36 | Example 37 |
|---|---|---|---|---|---|---|
| | Polymerizable monomer (A) having an acidic group | MDP | 30 | 15 | 15 | 15 |
| | Polymerizable monomer (B) having a fluorocarbon group | 8FMA | 2 | 2 | 2 | 2 |
| | Polymerizable monomer (E) having one polymerizable group and at least one hydroxyl group | HEMA | 18 | 37 | 28 | 32 |
| | Polymerizable monomer (F) having two polymerizable groups and two hydroxyl groups | GEDMA | 10 | 5 | 14 | 10 |
| | Crosslinkable polymerizable monomer (G) | Bis-GMA | 40 | 41 | 41 | 41 |
| | Water (C) | Distilled water | 20 | 20 | 20 | 20 |
| | Organic solvent (H) | Ethanol | 20 | 20 | 20 | 20 |
| | Polymerization initiator (D) | TMDPO | | | | |
| | | BAPO | 2 | 2 | 2 | 2 |
| | | CQ | 2 | 2 | 2 | 2 |
| | Polymerization accelerator (I) | PDE | 2 | 2 | 2 | 2 |
| | | DEPT | 2 | 2 | 2 | |
| | | TTA | | | | 2 |
| | Filler (J) | Inorganic filler 1 | 10 | 10 | 10 | 10 |
| | Bond strength to dentin (MPa) | After 24 hours | 16.9 | 19.3 | 19.2 | 17.4 |
| | | After thermal cycles | 16.2 | 19.5 | 19.4 | 16.3 |
| | Micro-tensile bond strength to dentin (MPa) | After 24 hours | 52.6 | 58.3 | 57.9 | 53.9 |
| | | After load applied | 51.9 | 57.6 | 56.8 | 51.0 |
| | Uniformity | | Uniform | Uniform | Uniform | Uniform |
| | Water absorption ratio of bond cured product (%) | | 8.2 | 7.2 | 7.1 | 6.9 |
| | Coloration of bond cured product | | Light yellow | Light yellow | Light yellow | Light yellow |
| | Sensitivity to ambient light | | 50 seconds | 50 seconds | 50 seconds | 50 seconds |

*The amounts of respective components added are indicated in the unit of parts by weight.

As shown in Tables 1 to 3, each one-part dental adhesive composition of the present invention had high bond strength to dentin, high micro-tensile bond strength, satisfactory uniformity and high stability to ambient light. Also, each bond cured product had low water absorption rate and minor coloration.

On the other hand, in Comparative Example 1 in which the polymerizable monomer (B) having a fluorocarbon group was not included, the adhesive property, uniformity and stability to ambient light were excellent, but the bond cured product had a high water absorption rate, the bond strength to dentin after the thermal cycles was reduced, and the degree of coloration was high. In Comparative Example 2 in which the water (C) was not included, the bond strength was reduced because the decalcifying effect and the penetration effect were lower, and the stability to ambient light was low because the ratio of the polymerizable monomers in the composition was increased. In Comparative Example 3 in which the content of the polymerizable monomer (A) having an acidic group was low, the bond strength was reduced because the decalcifying effect was lower. In Comparative Examples 4 in which the content of the polymerizable monomer (A) having an acidic group was high, the compatibility among the polymerizable monomers, the water (C) and the organic solvent (H) was reduced and the resultant composition became nonuniform. In addition, the curability was poor, causing deterioration in the adhesive property, an increase in the water absorption rate, and coloration of the cured product. In Comparative Example 5 in which DPEPA19F was added instead of the polymerizable monomer (B) having a fluorocarbon group, the compatibility among the polymerizable monomers, the water (C) and the organic solvent (H) was reduced and the resultant composition became nonuniform. In addition, the high hydrophobicity of DPEPA19F caused the composition to have lower penetration effect, reducing the bond strength.

Industrial Applicability

The one-part dental adhesive composition of the present invention is useful for bonding a dental restorative material, such as a dental composite resin, a dental compomer and a dental resin cement, to a tooth structure.

The invention claimed is:

1. A one-part dental adhesive composition, comprising a polymerizable monomer (A) having an acidic group, a polymerizable monomer (B) having a fluorocarbon group of formula (1), water (C), and a polymerization initiator (D),
wherein
the polymerizable monomer (A) is the monofunctional polymerizable monomer having a phosphinyl group in the molecule,
the polymerization initiator (D) is a bisacylphosphine oxide of formula (3),
a content of the polymerizable monomer (A) having an acidic group is from 5.5 to 35 parts by weight in 100 parts by weight of the total amount of polymerizable monomers,
formula (1) is

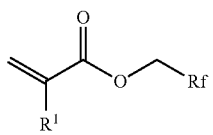

(1)

wherein R¹ denotes a hydrogen atom or a methyl group, and Rf denotes a fluoroalkyl group having 1 to 10 carbon atoms, and
formula (3) is

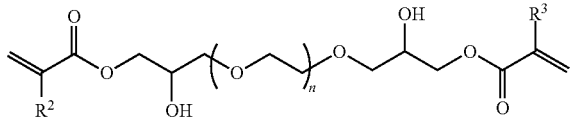

(2)

wherein R⁴ denotes an alkyl group, an alkenyl group, an alkynyl group, an aryl group, an alkoxy group, an acyl group or an acyloxy group, and
R⁵ to R¹⁴ each independently denote a hydrogen atom, a halogen atom, an alkyl group, an alkenyl group, an alkynyl group, an aryl group, an alkoxy group, an acyl group or an acyloxy group;
wherein a content of the polymerizable monomer (B) having a fluorocarbon group is from 0.5 to 10 parts by weight in 100 parts by weight of the total amount of polymerizable monomers.

2. The one-part dental adhesive composition according to claim 1, further comprising 10 to 50 parts by weight of a polymerizable monomer (E) having one polymerizable group and at least one hydroxyl group in 100 parts by weight of the total amount of polymerizable monomers.

3. The one-part dental adhesive composition according to claim 1, further comprising a polymerizable monomer (F) having two polymerizable groups and two hydroxyl groups of formula (2):

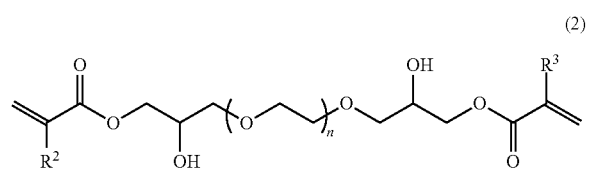

(2)

wherein R² and R³ each denote independently a hydrogen atom or a methyl group, and n denotes an integer of 1 to 5.

4. The one-part dental adhesive composition according to claim 3, wherein a content of the polymerizable monomer (F) is from 5 to 20 parts by weight in 100 parts by weight of the total amount of polymerizable monomers.

5. The one-part dental adhesive composition according to claim 1, further comprising 20 to 60 parts by weight of a crosslinkable polymerizable monomer (G), in 100 parts by weight of the total amount of polymerizable monomers,
wherein the crosslinkable polymerizable monomer (G) is at least one selected from the group consisting of an aromatic compound-based bifunctional polymerizable monomer, an aliphatic compound-based bifunctional polymerizable monomer, and trifunctional or higher polymerizable monomers, and
the aliphatic compound-based bifunctional polymerizable monomer is at least one selected from the group consisting of glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, polyethylene glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, and 2,2,4-trimethylhexamethylenebis(2-carbamoyloxyethyl) dimethacrylate.

6. The one-part dental adhesive composition according to claim 1, wherein a content of the polymerization initiator (D) is from 0.001 to 20 parts by weight with respect to 100 parts by weight of the total amount of polymerizable monomers.

7. The one-part dental adhesive composition according to claim 1, comprising an organic solvent (H).

8. The one-part dental adhesive composition according to claim 1, comprising a polymerization accelerator (I).

9. The one-part dental adhesive composition according to claim 1, comprising a filler (J).

* * * * *